(12) United States Patent
Baxter, Jr.

(10) Patent No.: US 6,185,988 B1
(45) Date of Patent: Feb. 13, 2001

(54) ANTI-FOULING APPARATUS FOR MARINE APPLICATIONS

(76) Inventor: John Francis Baxter, Jr., 1083 N. Collier #248, Marco Island, FL (US) 34145

(*) Notice: Under 35 U.S.C. 154(b), the term of this patent shall be extended for 0 days.

(21) Appl. No.: 09/549,939

(22) Filed: Apr. 14, 2000

(51) Int. Cl.$^7$ .................................................. G01N 33/18
(52) U.S. Cl. ........................................ 73/53.01; 73/866.5
(58) Field of Search .............................. 73/53.01, 64.56, 73/291, 863.01, 863.81, 863.82, 863.85, 866.5, 170.29; 210/747, 91, 104, 148, 241, 244, 246

(56) References Cited

U.S. PATENT DOCUMENTS

| | | | |
|---|---|---|---|
| 2,255,369 | * | 9/1941 | Spaeth ............................... 73/863.85 |
| 4,157,657 | * | 6/1979 | Hinchman ........................... 73/53.01 |
| 4,892,445 | * | 1/1990 | Paige ..................................... 405/224 |
| 5,186,050 | * | 2/1993 | Lagace et al. ....................... 73/866.5 |
| 5,299,141 | * | 3/1994 | Hungerford et al. .............. 73/863.01 |
| 5,816,874 | * | 10/1998 | Juran et al. ............................... 441/1 |

OTHER PUBLICATIONS

Omni Controls, Inc., Water Quality Sensors, http://www.omnicontrols.com/lists/quality.html, Mar. 28, 2000.

\* cited by examiner

*Primary Examiner*—Hezron Williams
*Assistant Examiner*—Michael Cygan
(74) *Attorney, Agent, or Firm*—Anton J. Hopen; Ronald E. Smith; Smith & Hopen, P.A.

(57) ABSTRACT

An apparatus for monitoring water quality parameters is protected from the deleterious effects of its environment when water quality is not being monitored. In a preferred embodiment, a sensor is mounted to a leading end of an elongate worm gear that is mounted in a housing that is positioned above the water level of the body of water under study. An output shaft of a reversible motor engages the worm gear so that the worm gear and sensor are displaced in a first direction when the output shaft rotates in a first direction and are displaced in a second, opposite direction, when the output shaft rotates in a second direction. A hingedly mounted door closes an open end of the housing and is biased to a closed position when a bias member is in repose. When the worm gear is extended, it pushes the door open and the door closes under its bias when the worm gear is retracted. When the worm gear is fully retracted, the sensor is protected by the housing. In this way, the sensor is subjected to the effects of the environment only during brief periods of actual immersion in the water when data is collected. This substantially lowers the cost of maintaining the sensor in good working order relative to the cost of maintaining a sensor that is continuously immersed. The apparatus may be mounted to a piling, a buoy, or any other structure that enables mounting of the apparatus in a predetermined spatial relation to the water line.

10 Claims, 4 Drawing Sheets

FIG. 1
FIG. 2
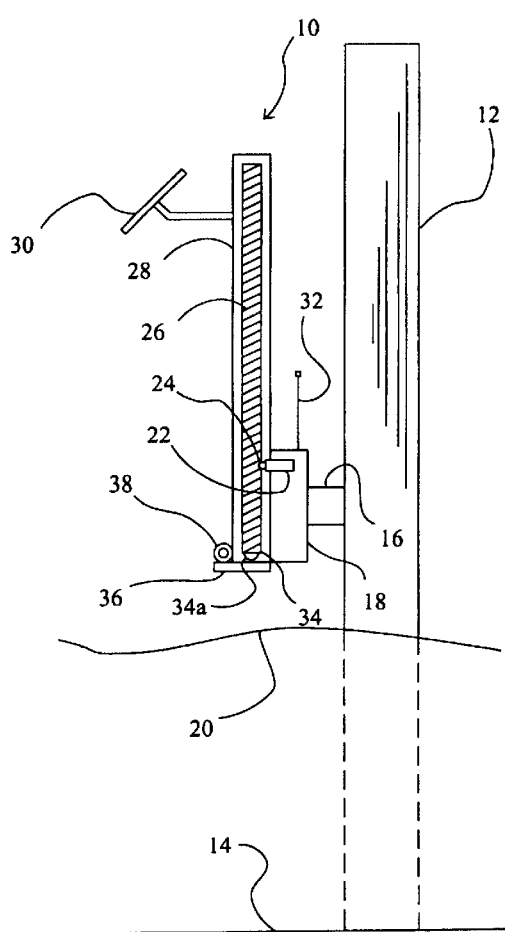
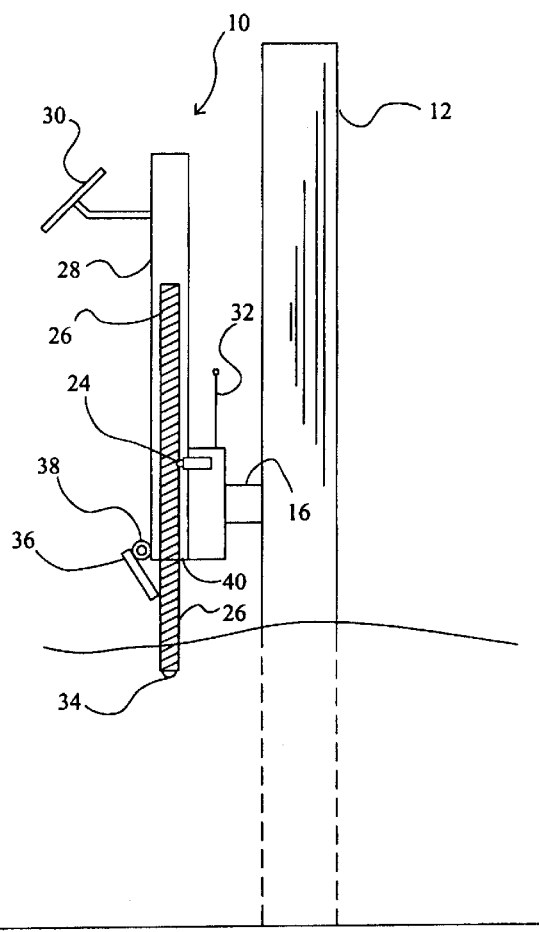

ANTI-FOULING APPARATUS FOR MARINE APPLICATIONS

BACKGROUND OF THE INVENTION

1. Field of the Invention

This invention relates, generally, to data-gathering devices that are used in marine environments. More particularly, it relates to means for protecting such devices from the effects of water exposure.

2. Description of the Prior Art

Untended monitoring devices for sensing, recording, and reporting various environmental conditions are well known. Recent advances include a fiber-optic sensor for the measurement of dissolved $CO_2$ in seawater currently under development by YSI, Inc., of Yellow Springs, Ohio. The YSI buoys used in marine environments are multi-parameter buoys; in addition to monitoring levels of dissolved $CO_2$, they also monitor dissolved oxygen pH, $pCO_2$, water temperature, conductivity, wind speed and direction, solar radiation, air temperature, and the like.

Nor are water quality monitoring devices restricted to seawater applications. They have utility in monitoring water quality parameters in wastewater, drinking water, aquaculture, surface water, groundwater, and estuaries as well.

Another company active in this industry is WET Labs, Inc., of Philonsth, Oreg. It provides underwater optical instrumentation for physical, biological, geological, and chemical characterization of the natural environment. The sensors made by WET Labs, Inc. perform the functions of spectrophotometry, and measure absorption, attenuation, scattering and fluorescence.

Unfortunately, monitoring devices dedicated to marine environments are subjected to the dilatory effects thereof, including corrosion, barnacles, algae, and the like. If a sensor dedicated to monitoring environmental conditions in the sea is exposed for sustained periods of time to the marine environment that it monitors, its useful life is short. Since marine sensors are often mounted in remote, not easily accessible locations, a long useful lifetime is desirable. Moreover, marine sensors may also be expensive, thereby providing another reason why a long service lifetime is preferred.

One way to extend the lifetime of a sensor in a marine environment is to perform a high level of maintenance on the sensor. Frequent removal of barnacles, for example, is mandatory if an ocean-based sensor is to have a commercially acceptable lifetime. Obviously, such frequent cleaning is labor intensive and accordingly quite expensive.

What is needed, then, is an inexpensive means for extending the operative lifetime of a water quality sensor.

However, in view of the prior art taken as a whole at the time the present invention was made, it was not obvious to those of ordinary skill in the pertinent art how these needs could be fulfilled.

SUMMARY OF THE INVENTION

The longstanding, but heretofore unfulfilled need for a low-maintenance sensor used in marine environments that has a long service lifetime is now met by a new, useful, and nonobvious invention. The antifouling apparatus of this invention includes a sensor means having a first, retracted position disposed above a water level of a body of water to be monitored. The sensor means has a second, extended position where it is disposed in immersed relation to the body of water. A retraction and extension means selectively extends and retracts the sensor means relative to a housing that is mounted above the water level. Significantly, the sensor means is extended and immersed in the body of water only during a predetermined amount of time required to make a measurement of a preselected water quality parameter, i.e., the sensor means is retracted and out of contact with the body of water when no measurement is being made. Thus, the sensor means undergoes the deleterious effects caused by the body of water to a much lesser extent than sensor means that are in continuous contact with a body of water.

The sensor means is disposed wholly within the housing means when in its first, retracted position and it is at least partially outside the housing means when in its second, extended position.

An imperforate door means is provided for opening and closing the housing means. The door means is open when the sensor means is in its second, extended position and the door means is closed when the sensor means is in its first, retracted position.

A bias means maintains the door means in a normally closed position when the bias means is in a position of repose.

The retraction and extension means may take many forms. In a preferred embodiment, it includes an elongate worm gear that is meshingly engaged by an output shaft of a preselected reversible motor means. The sensor means is mounted on a leading end of the worm gear. Rotation of the output shaft in a first direction displaces the worm gear into its first, retracted position and rotation of the output shaft in a second direction, opposite to the first direction, displaces the worm gear into its second, extended position.

A control means controls operation of the motor means. In the preferred embodiment, an antenna means receives signals from a remote location for activating and deactivating the motor means. The antenna means also forms part of a transmission means for reporting data gathered by the sensor means to a remote site for collecting said data.

Alternatively, a timer means at the site of the monitoring apparatus may be employed for activating and deactivating the motor means at predetermined times.

It is therefore clear that the primary object of this invention is to provide a water quality monitoring apparatus for use in marine environments that is substantially protected from the deleterious effects of the environment within which it is used.

More specific objects are to provide a means for mounting a sensor in spaced apart relation to a body of water, and to provide means for deploying the sensor into operable relation to the water for only as much time as is required to sense one or more preselected water qualities.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a side elevational view depicting a first embodiment of the novel apparatus when a sensor means is in its retracted position; and FIG. 2 is a side elevational view depicting the sensor means of FIG. 1 in its extended position.

DETAILED DESCRIPTION OF THE PREFERRED EMBODIMENT

Figure 2A:
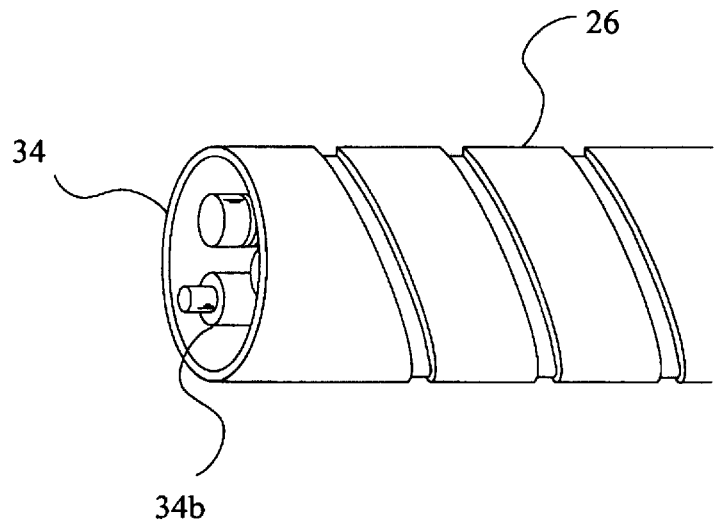
FIG. 2A is a side elevational view of an alternative, recessed mounting for the sensor means.

Referring now to FIG. 1, it will there be seen that an illustrative embodiment of the present invention is denoted as a whole by the reference numeral 10.

Figure 4:
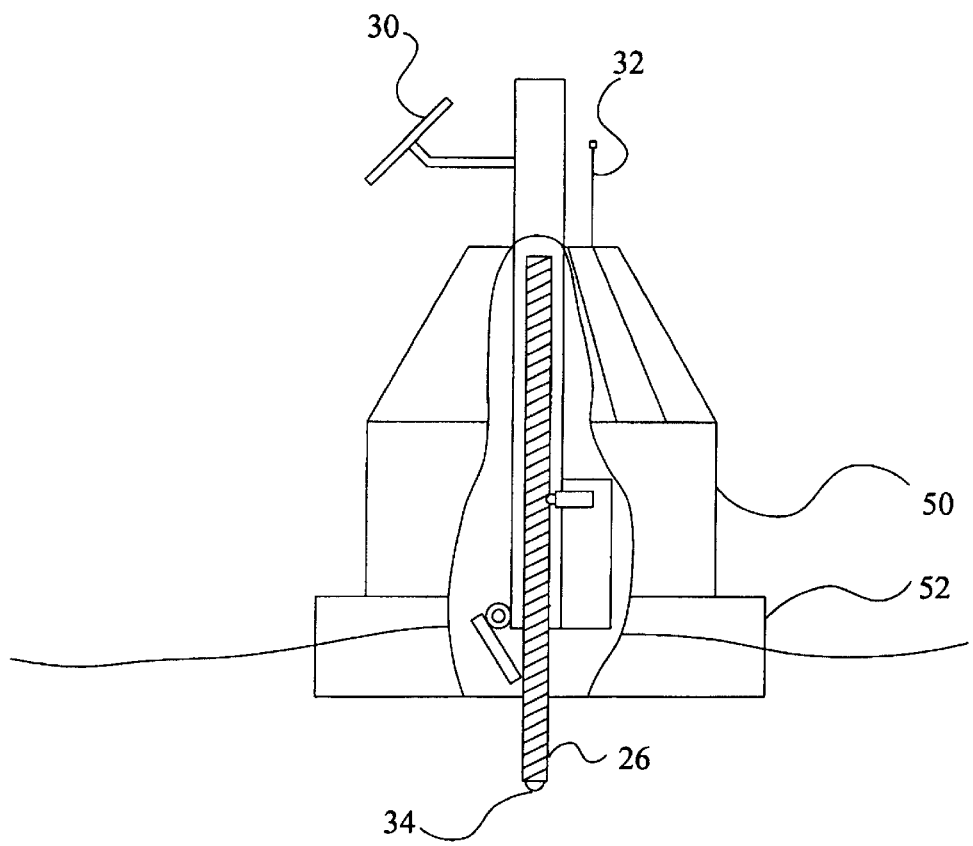
FIG. 4 is a partially sectioned, side elevational view of an alternative mounting for the novel apparatus.
Figure 5:
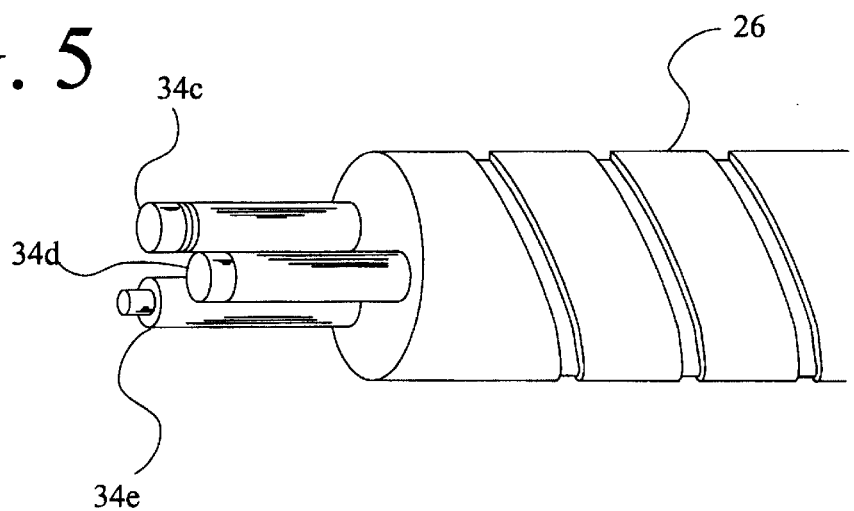
FIG. 5 is an isometric view of a plurality of sensor means extending from an elongate worm gear.

In a first embodiment, novel apparatus 10 is adapted to be mounted to a stationary piling 12 mounted in a seabed 14. It may also be mounted on any other structure as long as it is spaced above the water level. Although depicted in a vertical orientation in FIGS. 1 and 2, it should be understood that the novel apparatus may be mounted at any predetermined angle relative to a vertical plane, the only restriction being that a horizontal mounting would not be employed in connection with an open body of water. For example, a buoy having a toroidal base might collect contaminates within the area surrounded by the base, so a vertical mounting of the novel apparatus on such a buoy is contraindicated. In such an environment, the apparatus to be disclosed is mounted at a forty-five degree or other suitable angle to cause the sensor means, when deployed, to become immersed outside the confines of the base of the buoy. Alternatively, when sensor means are deployed at a sufficient depth, or such sensor means are resistant to false readings from contaminates surrounding the base, a vertical mounting may be deployed as illustrated in FIG. 4.

In the vertically-oriented embodiment of FIGS. 1 and 2, a stand-off 16 is fixedly secured to piling 12 and interconnects control box 18 to said piling at a preselected point above water line 20.

A battery-powered reversible motor means 22 having an output shaft 24 is mounted in the control box to protect it from the marine environment. Output shaft 24 is in meshing engagement with an elongate worm gear 26 that is mounted for rotation in housing 28. A suitable opening is formed in the abutting walls of control box 18 and housing 28 to enable the engagement of said worm gear 26 by said output shaft 24.

Solar panel 30, preferably mounted on housing 28, provides power to re-charge the batteries, not shown, that provide the motive force for operating motor means 22.

Motor means 22 may be timer-controlled to activate at predetermined intervals, or it may be activated by electromagnetic signals from a remote location that induce voltages in antenna 32, said signals being generated at a predetermined assigned frequency by the authority owning novel apparatus 10.

When motor means 22 is activated, output shaft 24 rotates in a first predetermined direction and drives worm gear 26 in a first direction, towards the water. The leading end 34 of worm gear 26 bears against and opens a normally closed closure means in the form of a spring-loaded, normally closed imperforate door 36, as best understood by comparing FIGS. 1 and 2. In this exemplary embodiment, the reference numeral 38 denotes a spring-loaded hinge having a position of repose that maintains door 36 in its FIG. 1 position when worm gear 26 is in its retracted configuration.

In the depicted, preferred embodiment, sensor means 34a is mounted on the leading end 34 of worm gear 26. Sensor means 34a is of the type that senses predetermined qualities of the water within which it immersed.

In the alternative embodiment of FIG. 2A, sensor means 34b is set back from leading end 34 so that said sensor 34a does not make physical contact with door 36.

Upon detection of a second signal, motor means 22 operates in a reverse direction so that the rotation of output shaft 24 causes retraction of worm gear 26 back into housing 28. The leading edges of door 36 are suitably rounded so as not to prevent such retraction, and the self-bias of hinge 38 closes door 36 when the worm gear is fully retracted.

In this way, sensor 34a or 34b is exposed to the marine environment only during its actual working time. Thus, it will be immersed only a few minutes a day or week, depending upon its duty cycle, instead of twenty four hours a day as in prior art devices.

Imperforate door 36 may be provided with a suitable gasket or other sealing means about its peripheral edges to further inhibit sea water from entering housing 28 even under high wind and wave conditions.

A wiper means 40 (FIG. 2) could be mounted at the lowermost end of housing 28 to dry worm gear 26 as it is retracted into said housing.

Figure 3:
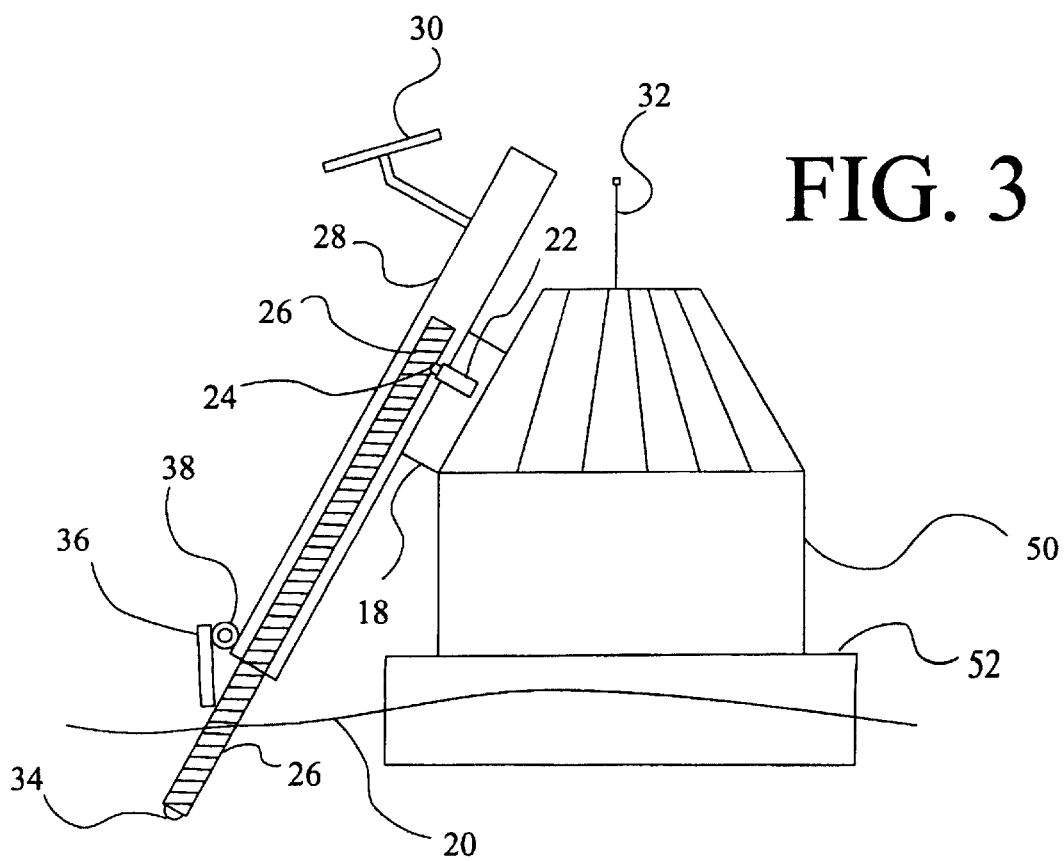
FIG. 3 is a side elevational view of an alternative mounting for the novel apparatus.

An alternative mounting for novel apparatus 10 is depicted in FIG. 3. Buoy 50 has a toroidal base 52 so a mounting of apparatus 10 where it is coincident with the vertical axis of symmetry of said buoy 50 is contraindicated for the reasons mentioned earlier. Accordingly, control box 18 is mounted to an inclined surface of said buoy as depicted so that sensor means 34 samples water that is not within the toroidal space bounded by base 52. A stand-off would be used if it was not feasible to mount control box 18 directly to the buoy as depicted. FIG. 4 illustrates an alternative embodiment wherein the leading end is immersed to a sufficient depth to avoid an abnormally high concentration reading of accumulated substances within the toroidal base 52.

Figure 6:
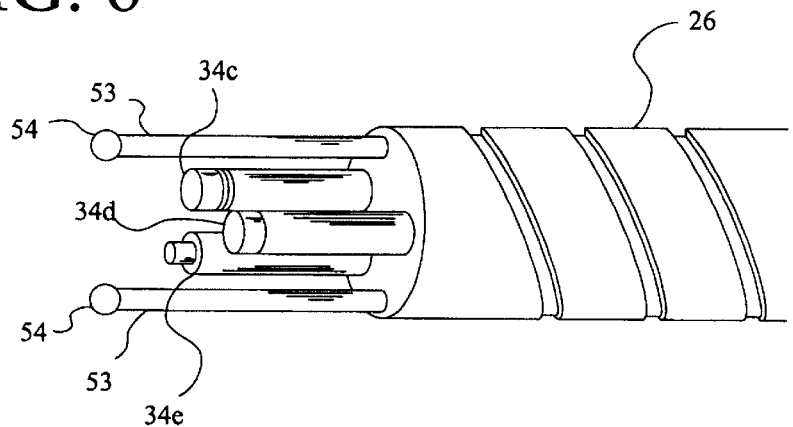
FIG. 6 is an isometric view of a plurality of sensor means and a pair of elongate members in leading relation to the plurality of sensor means extending from an elongate worm gear.
Figure 7:
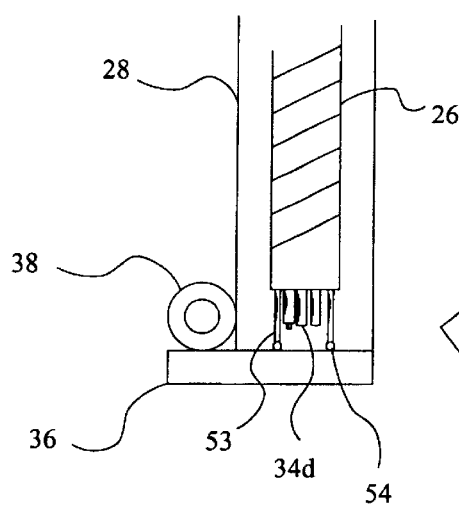
FIG. 7 is a side elevational view of the elongate members abutting the door means in a closed position.
Figure 8:
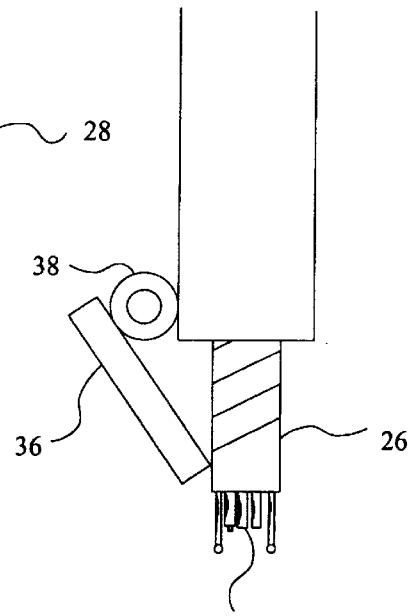
FIG. 8 is a side elevational view of the elongate members abutting the door means in a partially open position.
Figure 9:
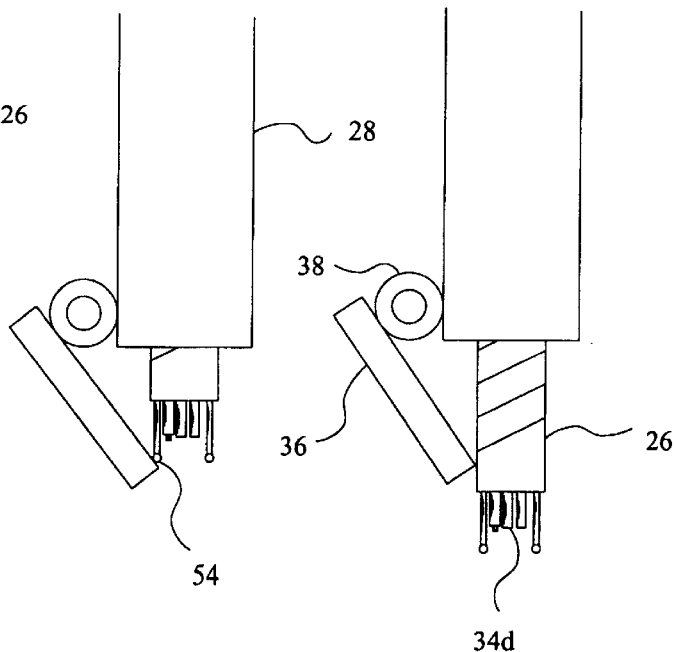
FIG. 9 is a side elevational view of the elongate members extended beyond contact with the door means which is in a fully open position.

FIG. 6 shows a pair of substantially rigid elongate members 53 in leading relation to a plurality of sensors 34c–e. A leading contact point 54 abuts the imperforate door 36 thereby preventing the plurality of sensors 34c–e and the imperforate door 36 from coming into contact. FIGS. 7–9 illustrate the mechanism of the elongate members 53 abutting the imperforate door 36 as the worm gear 26 drives the sensors 34c–e downward. The imperforate door 36 is pushed downward and open without contacting the sensors 34c–e. While a single elongate member 53 may be used to achieve this result, at least two or more elongate members 53 is leading relation to the sensors 34c–e is preferred.

Those having skill in the art of machine design will be able to construct numerous alternative mechanisms for causing the controlled retraction and extension of the sensor means. A worm gear reciprocated by the output shaft of a reversible motor is only one of many mechanisms that can embody this invention. Accordingly, all such mechanical means are within the scope of this invention because the invention includes a water quality sensor that is spaced apart from a body of water when not performing a monitoring function and which is operably immersed within said body of water only during such time a measurement is being taken. Thus, it should be understood that the means for accomplishing the retraction and extension of the sensor means is of secondary importance. Equivalent retraction and extension means would include telescoping structures, accordion or bellows-like structures, jointed, expandable linkages, rack and pinion assemblies, and the like. Alternative motive forces could be supplied by hydraulic means, air pressure, and so on.

It will be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. An apparatus for monitoring water quality, comprising:
   a sensor means having a first, retracted position disposed above a water level of a body of water to be monitored;
   said sensor means having a second, extended position where it is disposed in immersed relation to said body of water;
   retraction and extension means for selectively extending and retracting said sensor means;
   said sensor means capable of being extended and immersed in said body of water only during a predetermined amount of time required to make a measurement of a preselected water quality parameter;
   said sensor means capable of being retracted and out of contact with said body of water when no measurement is being made;
   a housing means for said sensor means, said sensor means being disposed wholly within said housing means when said sensor means is in said first, retracted position and said sensor means being disposed wholly outside said housing means when said sensor means is in its second, extended position;
   a door means for opening and closing said housing means, said door means being open when said sensor means is in said second, extended position and said door means being closed when said sensor means is in said first, retracted position;
   a bias means for maintaining said door means in a normally closed position when said sensor means is in said first, retracted position; and
   at least one elongate member positioned in leading relation to said sensor means wherein said at least one elongate member abuts and pushes open said door means thereby preventing said sensor means from contacting said door means when said sensor means is extended from said first to said second position;
   whereby said sensor means undergoes the deleterious effects of said body of water to a lesser extent than sensor means that are in continuous contact with said body of water.

2. The apparatus of claim 1, wherein said retraction and extension means includes an elongate worm gear that is meshingly engaged by an output shaft of a preselected motor means, wherein said sensor means is mounted on a leading end of said worm gear, wherein rotation of said output shaft in a first direction displaces said worm gear into said first, retracted position and wherein rotation of said output shaft in a second direction, opposite to said first direction, displaces said worm gear into said second, extended position.

3. The apparatus of claim 2, further comprising a control means for controlling operation of said motor means, and an antenna means for receiving signals from a remote location for activating and deactivating said motor means, said antenna means also forming part of a transmission means for reporting data gathered by said sensor means to a preselected remote site for collecting said data.

4. The apparatus of claim 2, further comprising a timer means for activating and deactivating said motor means at predetermined times, and a transmission means for transmitting data gathered by said sensor means to a preselected remote site for collecting data.

5. The apparatus of claim 1, wherein said apparatus is mounted in a vertical plane.

6. The apparatus of claim 5, wherein said apparatus is mounted to a piling that is disposed in upstanding relation relative to a sea bed.

7. The apparatus of claim 1, wherein said apparatus is mounted at a predetermined angle relative to a vertical plane.

8. The apparatus of claim 1, wherein said apparatus is mounted to a buoy having a base that surrounds a predetermined area of water, and wherein mounting said apparatus at said predetermined angle positions said sensor means outside of said surrounded area.

9. The apparatus of claim 5, wherein said apparatus is mounted to a buoy having a base that surrounds a predetermined area of water, and wherein mounting said apparatus in said vertical plane positions said sensor means inside of said surrounded area.

10. An apparatus for monitoring water quality, comprising:
   a sensor means having a first, retracted position disposed above a water level of a body of water to be monitored;
   said sensor means having a second, extended position where it is disposed in immersed relation to said body of water;
   said sensor means being capable of being extended and immersed in said body of water only during a predetermined amount of time required to make a measurement of a preselected water quality parameter;
   said sensor means being capable of being retracted and out of contact with said body of water when no measurement is being made;
   a first housing means for said sensor means, said sensor means being disposed wholly within said first housing means when said sensor means is in said first, retracted position and said sensor means being disposed wholly outside said first housing means when said sensor means is in its second, extended position;

said first housing means having a first end positioned in remote relation to said body of water and a second end positioned in a spaced apart relation to said body of water that is closer thereto than said first end;

a door means for opening and closing said first housing means, said door means being open when said sensor means is in said second, extended position and said door means being closed when said sensor means is in said first, retracted position;

said door means being hingedly mounted to said second end of said first housing means;

a bias means for maintaining said door means in a normally closed position when said sensor means is in said first, retracted position;

a worm gear rotatably mounted within said first housing means;

said worm gear having a leading end and a trailing end, said leading end being disposed within said first housing means when said sensor means is in its first, retracted position and said leading end being disposed outside said first housing means when said sensor means is in its second, extended position;

said door means being in an open position and being held open by said worm gear when said sensor means is in its extended, immersed position;

said sensor means being mounted on said leading end of said worm gear;

a reversible motor means having an output shaft disposed in meshing engagement to said worm gear so that rotation of said worm gear in a first direction effects retraction of said sensor means into said housing and so that rotation of said worm gear in a second direction effects extension of said sensor means out of said first housing means and into immersed relation to said body of water;

a second housing means for housing said reversible motor means;

said second housing means being mounted to said first housing means;

whereby when said sensor means is in its retracted position, said door is closed and said sensor is protectively housed within said first housing means, out of said immersed relation to said body of water;

whereby said sensor means is not subjected to the debilitating effects of said body of water when said sensor means is in said first, retracted position.

* * * * *